(12) United States Patent
Rothschild

(10) Patent No.: US 8,155,887 B2
(45) Date of Patent: Apr. 10, 2012

(54) COMPUTER VISUALIZED DRUG INTERACTION INFORMATION RETRIEVAL

(75) Inventor: Leigh M. Rothschild, Sunny Isles, FL (US)

(73) Assignee: SRR Patent Holdings, LLC, Sunny Isles Beach, FL (US)

( * ) Notice: Subject to any disclaimer, the term of this patent is extended or adjusted under 35 U.S.C. 154(b) by 809 days.

(21) Appl. No.: 12/191,759

(22) Filed: Aug. 14, 2008

(65) Prior Publication Data

US 2010/0042395 A1    Feb. 18, 2010

(51) Int. Cl.
*G06F 7/00*     (2006.01)
(52) U.S. Cl. ............... 702/19; 702/20; 703/11; 707/700
(58) Field of Classification Search ................... None
See application file for complete search history.

(56) References Cited

U.S. PATENT DOCUMENTS 7,154,102 B2 * 12/2006 Poteet et al. .................. 250/372
7,469,213 B1 * 12/2008 Rao .................................. 705/2

* cited by examiner

Primary Examiner — Mary Zeman
(74) Attorney, Agent, or Firm — Cuenot, Forsythe & Kim, LLC

(57) ABSTRACT

Embodiments of the present invention provide a method, system and computer program product for computer visualization of drugs for drug interaction information retrieval. In an embodiment of the invention, a method for computer visualization of drugs for drug interaction information retrieval can be provided. The method can include acquiring imagery of multiple different substances and detecting identifying content in each acquired image to determine an identity of each substance corresponding to each acquired image. The method also can include retrieving drug interaction data for each substance using the determined identity and correlating the drug interaction data for at least one of the substances with at least one other of the substances. Finally, the method can include displaying the correlated drug interaction data.

13 Claims, 2 Drawing Sheets

COMPUTER VISUALIZED DRUG INTERACTION INFORMATION RETRIEVAL

BACKGROUND OF THE INVENTION

1. Field of the Invention

The present invention relates to the field of computerized drug identification and more particularly to computer aided visualization for drug identification.

2. Description of the Related Art

Prescription drug use has become part and parcel of modern society. Though medicinal compositions have always been dispensed for what ails and even for what does not ail, governmental regulation of food and drugs in recent years has resulted in the consolidation of medicinal compositions into two classes of drugs—those that require a prescription and those that do not. Recent advances in technology have made available many drugs formerly requiring a prescription as "over-the-counter" medications requiring no prescription at all. In many cases, over-the-counter versions of a prescription drug are no more than weakened forms of the prescription drug. In any event, the widespread availability of drugs, both prescription and over-the-counter, has resulted in a substantial population of patients consuming multiple different types of drugs at any given time.

Drug interactions remain a principal aspect of the pharmaceutical sciences. A drug interaction is a commonly known situation in which a substance affects the activity of a drug, such that the effects of a given drug is increased or decreased, or the combination of the substance and the drug produce a new effect that neither produces alone. Typically, drug-drug interactions are most unpredictable; however, drug-food interactions also are known to exist between drugs and foods, as well as drug-herb interactions between drugs and herbs.

Generally speaking, it is desirable to avoid drug interactions due to the possibility of a poor or unexpected outcome resulting from the interaction of a drug with another substance. Consequently, known drug interactions often are listed in the literature distributed with a drug. Providing an exhaustive list of drug interactions in literature, however, can be difficult when a substantial number of drug interactions are known to exist. As such, voluminous books have been created as an aggregation of known drug interactions. While the most diligent review of a book of known drug interactions will reveal the requisite information necessary to avoid an undesirable outcome from a drug interaction of a prescribed selection of drugs, in practice it is not reasonable to presume that a dispensary of drugs will consult the requisite literature when dispensing a drug.

BRIEF SUMMARY OF THE INVENTION

Embodiments of the present invention address deficiencies of the art in respect to drug interaction determination when dispensing a drug and provide a novel and non-obvious method, system and computer program product for computer visualization of drugs for drug interaction information retrieval. In an embodiment of the invention, a method for computer visualization of drugs for drug interaction information retrieval can be provided. The method can include acquiring imagery of multiple different substances and detecting identifying content in each acquired image to determine an identity of each substance corresponding to each acquired image. The method also can include retrieving drug interaction data for each substance using the determined identity and correlating the drug interaction data for at least one of the substances with at least one other of the substances. Finally, the method can include displaying the correlated drug interaction data. In this way, the relative drug interactions resulting from the dispensing of multiple different substances can be determined without requiring a tedious manual process of looking up drug interaction data for each substance and manually correlating the drug interaction data for the specific combination of dispensed substances.

In another embodiment of the invention, a data processing system can be configured for computer visualization of drugs for drug interaction information retrieval. The system can include a camera communicatively coupled to a host computing platform, a data store of drug image data communicatively coupled to the host computing platform and also a data store of drug interaction data communicatively coupled to the host computing platform. Of note, the data stores can reside within a single or multiple different databases. Notably, the system also can include computer visualization of drugs for drug interaction information retrieval logic executing in the host computing platform.

The logic can include program code enabled to acquire imagery of multiple different substances, to detect identifying content in each acquired image and to determine by reference to the data store of drug image data an identity of each substance corresponding to each acquired image, to retrieve drug interaction data from the data store of drug interaction data for each substance using the determined identity, to correlate the drug interaction data for at least one of the substances with at least one other of the substances, and to display the correlated drug interaction data through the host computing platform.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the present invention provide a method, system and computer program product for computer visualization of drugs for drug interaction information retrieval. In accordance with an embodiment of the present invention, multiple different drugs can be imaged to detect identifiable content disposed on the different drugs. Each image of each drug can be compared to a data store of drug information to identify each drug. Thereafter, drug interaction data can be retrieved for each identified drug. Further, known drug-drug interactions for the identified drugs can be determined and a report can be provided to include the known drug-drug interactions. In this way, drug-drug interactions resulting from the use of the multiple different drugs can be determined without recourse to a voluminous text of drug interactions.

Figure 1:
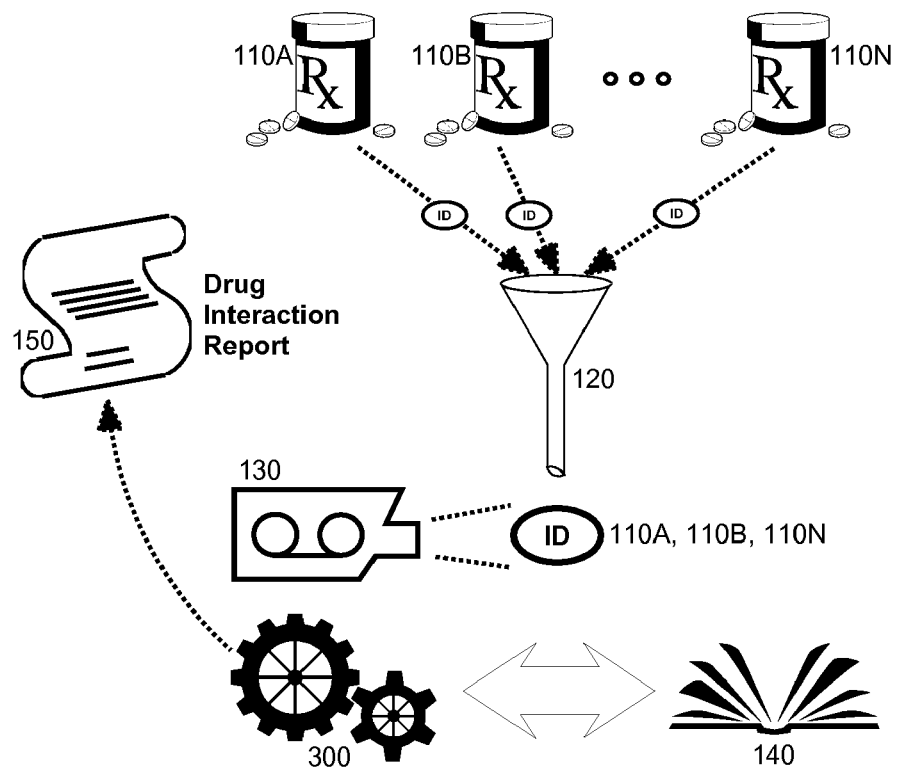
FIG. 1 is a pictorial illustration of a process for computer visualization of drugs for drug interaction information retrieval.

In illustration, FIG. 1 is a pictorial illustration of a process for computer visualization of drugs for drug interaction information retrieval. As shown in FIG. 1, multiple different substances 110A, 110B, 110N, whether prescription drugs, over-the-counter drugs or even vitamins and herbal remedies, can be provided to a marshalling apparatus 120 such as a gravity feed or miniature conveyor belt or even a chamber. The marshalling apparatus 120 can isolate an individual one of the different substances 110A, 110B, 110N for imaging by camera 130, for example a charge coupled device (CCD) driven digital camera or video recorder.

The camera 130 can capture an image of each individual one of the different substances 110A, 110B, 110N and computer visualization for drug interaction information retrieval logic 300 can process each captured image to detect identifying content disposed on each of the different substances 110A, 110B, 110N such as a pill marking or code. The computer visualization for drug interaction information retrieval logic 300 in turn can compare the identified content to a data store of known substances 140 to identify each of the different substances 110A, 110B, 110N. The computer visualization for drug interaction information retrieval logic 300 further can lookup not only known drug interactions for each of the different substances 110A, 110B, 110N, but also known drug interactions between the identified ones of the substances 110A, 110B, 110N. Thereafter, a drug interaction report 150 can be produced indicating the known drug interactions between the identified ones of the substances 110A, 110B, 110N.

Figure 2:
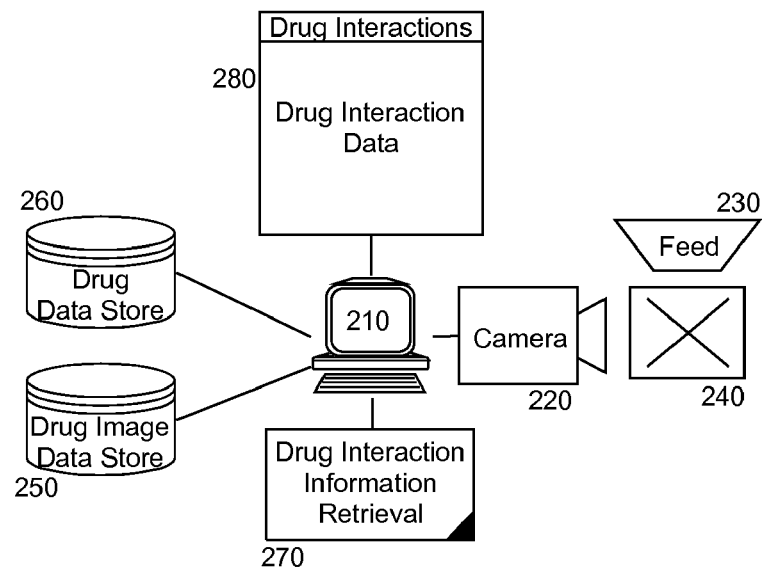
FIG. 2 is a schematic illustration of a data processing system configured for computer visualization of drugs for drug interaction information retrieval; and, FIG. 3 is a flow chart illustrating a process for computer visualization of drugs for drug interaction information retrieval.

The process shown in FIG. 1 can be implemented within a data processing system. In further illustration, FIG. 2 schematically depicts a data processing system configured for computer visualization of drugs for drug interaction information retrieval. The system can include a host computing platform 210 coupled to a camera 220 such as a digital still camera or digital video camera. The camera 220 can be focused on a marshalling point 240 provided by a marshalling apparatus 230, for example gravity feed or isolation chamber or miniature conveyor belt. The host computing platform 210 also can be communicatively coupled a drug image data store 250 of known substances and corresponding known identifying content visually disposed on the known substances. The host computing platform 210 additionally can be communicatively coupled to a drug interaction data store 260 providing drug interaction data for different substances relative to other substances including prescription and over-the-counter drugs, vitamins and herbal remedies, and food products.

Notably, the host computing platform 210 can support the execution of computer visualization for drug interaction information retrieval logic 270. The logic can include program code enabled to acquire imagery of different substances in the marshalling point 240. The program code further can be enabled to locate and retrieve identifying content disposed on the different substances and to look up the identifying content in the drug image data store 250 in order to identify each of the substances. The program code yet further can be enabled to retrieve from drug interaction data store 260 drug interactions for each of the identified substances and to particularly correlate the retrieved drug interactions to different ones of the substances so that relative drug interactions can be determined for the substances. Finally, the program code can be enabled to render a report of drug interaction data in a graphical user interface display 280 of drug interaction data.

It will be recognized by the skilled artisan that while the computer visualization for drug interaction information retrieval logic 270 is shown to execute in a single host computing platform 210, the invention is not so limited and the computer visualization for drug interaction information retrieval logic 270 also can be distributed in form across multiple different computing platforms. Further, the camera 220 and marshalling apparatus 230 can be located remotely from the host computing platform 210 whilst providing acquired imagery to the host computing platform 210 over a computer communications network, whether wireless or wirebound. Yet further, either or both of the drug image data store 250 and the drug interaction data store 260 can be remotely disposed from the host computing platform 210 and accessible over a computer communications network, whether wireless or wirebound.

Figure 3:
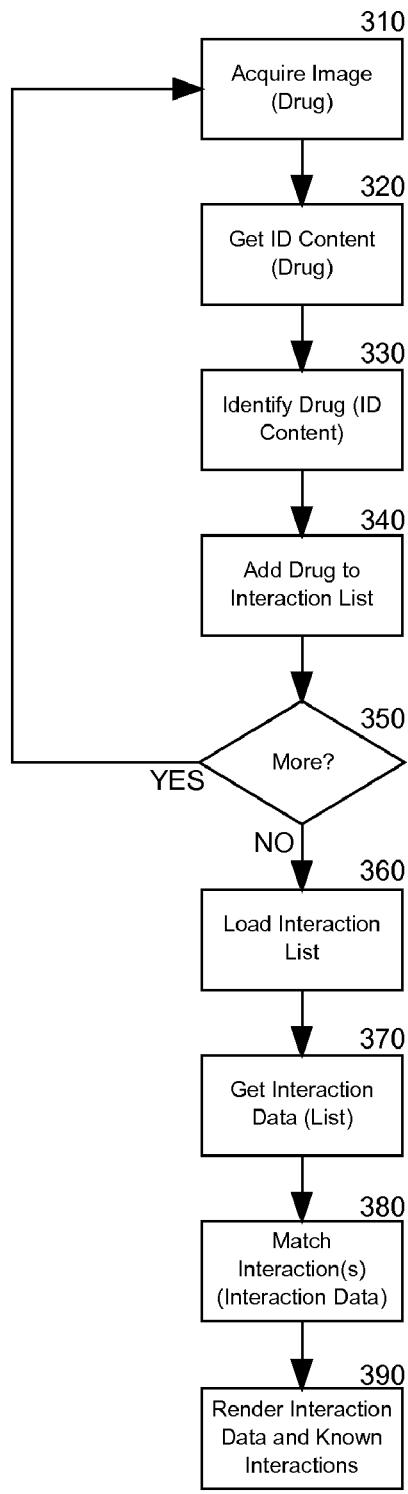

In yet further illustration of the operation of the computer visualization for drug interaction information retrieval logic 270, FIG. 3 is a flow chart illustrating a process for computer visualization of drugs for drug interaction information retrieval. Beginning in block 310, an image of a substance such as a drug can be acquired and in block 320, identifying content for the substance can be retrieved from the image. In block 330, the substance can be identified according to the identifying content and in block 340, the identified substance can be added to an interaction list. In decision block 350, if additional substances remain to be imaged, the process can repeat through block 310. Otherwise, the process can continue through block 360.

In block 360, the interaction list now populated by a list of imaged substances can be loaded for processing. In block 370, drug data and drug interaction data for each of the imaged substances in the list can be retrieved. Specifically, the drug data can include an expiration date for each of the imaged substances, usage instructions for each of the imaged substances, warnings provided if any for each of the imaged substances, contact information for a manufacturer of each of the imaged substances, a photograph or textual description of each of the imaged substances, as well as reorder information for each of the imaged substances.

In block 380, relative interactions between the different imaged substances can be determined by locating references in the interaction data for each of the imaged substances to others of the imaged substances. Finally, in block 390, the relative interactions can be rendered within a report such as a paper report or a graphical user interface display. Optionally, an activatable link can be provided in the display for selected ones of the imaged substances for reordering the selected ones of the imaged substances. In this way, the relative drug interactions resulting from the dispensing of multiple different substances can be determined without requiring a tedious manual process of looking up drug interaction data for each substance and manually correlating the drug interaction data for the specific combination of dispensed substances.

Embodiments of the invention can take the form of an entirely hardware embodiment, an entirely software embodiment or an embodiment containing both hardware and software elements. In a preferred embodiment, the invention is implemented in software, which includes but is not limited to firmware, resident software, microcode, and the like. Furthermore, the invention can take the form of a computer program product accessible from a computer-usable or computer-readable medium providing program code for use by or in connection with a computer or any instruction execution system.

For the purposes of this description, a computer-usable or computer readable medium can be any apparatus that can contain, store, communicate, or transport the program for use by or in connection with the instruction execution system, apparatus, or device. The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

I claim:

1. A computer-implemented method for computer visualization of drugs for drug interaction information retrieval, comprising:
   acquiring, for each of multiple different substances, imagery of at least one external characteristic of a physical body of the substance;
   determining an identity of each of the multiple different substances based upon the at least one external characteristic from the acquired imagery;
   retrieving drug interaction data for each of the multiple different substances using the determined identities;
   correlating, using a processor, drug interaction data for at least one of the multiple different substances with at least one other of the multiple different substances; and
   displaying the correlated drug interaction data.

2. The method of claim 1, further comprising
   marshalling the multiple different substances for individual imaging.

3. The method of claim 1, wherein
   the imagery of multiple different substances is imagery of multiple different drugs.

4. The method of claim 1, wherein
   individual drug interaction data is displayed for each of the multiple different substances.

5. A data processing system configured for computer visualization of drugs for drug interaction information retrieval, the comprising:
   a host computing platform
   a camera communicatively coupled to the host computing platform;
   a data store of drug image data communicatively coupled to the host computing platform; and
   a data store of drug interaction data communicatively coupled to the host computing platform, wherein
   the host computing platform is configured to
      acquire, for each of multiple different substances, images of at least one external characteristic of a physical body of the substance,
      determine an identity of each of the multiple different substances based upon the at least one external characteristic from the acquired imagery,
      retrieve the drug interaction data for each of the multiple different substances using the determined identities,
      correlate drug interaction data for at least one of the multiple different substances with at least one other of the multiple different substances, and
      display the correlated drug interaction data.

6. The system of claim 5, wherein
   the substances comprise at least one drug.

7. The system of claim 5, wherein
   the data store of drug image data and the data store of drug interaction data are disposed in a single database.

8. The system of claim 5, further comprising
   a marshalling apparatus configured to marshal the multiple different substances into a marshalling point for individual imaging by the camera.

9. The system of claim 8, wherein
   the marshalling apparatus is a gravity feed.

10. A computer program product comprising a computer usable storage medium having stored therein computer usable program code for computer visualization of drugs for drug interaction information retrieval, the computer usable program code, which when executed by a computer hardware system, causes the computer hardware system to perform
   acquiring, for each of multiple different substances, imagery of at least one external characteristic of a physical body of the substance;
   determining an identity of each of the multiple different substances based upon the at least one external characteristic from the acquired imagery;
   retrieving drug interaction data for each of the multiple different substances using the determined identities;
   correlating drug interaction data for at least one of the multiple different substances with at least one other of the multiple different substances; and
   displaying the correlated drug interaction data.

11. The computer program product of claim 10, wherein the computer usable program code further causes the computer hardware system to perform
   marshalling the multiple different substances for individual imaging.

12. The computer program product of claim 10, wherein
   the imagery of multiple different substances is imagery of multiple different drugs.

13. The computer program product of claim 10, wherein
   individual drug interaction data is displayed for each of the multiple different substances.

* * * * *